United States Patent
Hirano et al.

(10) Patent No.: US 6,816,573 B2
(45) Date of Patent: Nov. 9, 2004

(54) X-RAY GENERATING APPARATUS, X-RAY IMAGING APPARATUS, AND X-RAY INSPECTION SYSTEM

(75) Inventors: Masayuki Hirano, Hamamatsu (JP); Hiroki Kawakami, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 09/943,085

(22) Filed: Aug. 31, 2001

(65) Prior Publication Data

US 2002/0034279 A1 Mar. 21, 2002

Related U.S. Application Data

(63) Continuation-in-part of application No. PCT/JP00/01238, filed on Mar. 2, 2000.

(30) Foreign Application Priority Data

Mar. 2, 1999 (JP) .......................................... P11-054267

(51) Int. Cl.[7] .................................................. H05G 1/56
(52) U.S. Cl. ...................... 378/114; 378/101; 378/102; 378/103; 378/104; 378/105; 378/106; 378/110; 378/111; 378/121; 378/136; 378/138; 363/17; 363/25; 363/26
(58) Field of Search ................................. 378/101–106, 378/110–114, 136, 138, 121; 363/17, 25–26

(56) References Cited

U.S. PATENT DOCUMENTS 4,734,924 A * 3/1988 Yahata et al. ................ 315/107

| | | | |
|---|---|---|---|
| 5,077,771 A | 12/1991 | Skillicorn et al. | 378/102 |
| 5,398,274 A | 3/1995 | Komatani et al. | 378/98 |

FOREIGN PATENT DOCUMENTS

| | | |
|---|---|---|
| FR | 2 718 599 | 10/1995 |
| GB | 1 428 305 | 3/1976 |
| JP | 62-188148 | 8/1987 |
| JP | 64-33899 | 2/1989 |
| JP | 2-297850 | 12/1990 |
| JP | 5-188018 | 7/1993 |
| JP | 8-178872 | 7/1996 |

* cited by examiner

Primary Examiner—Robert H. Kim
Assistant Examiner—George Y. Wang
(74) Attorney, Agent, or Firm—Morgan, Lewis & Bockius LLP

(57) ABSTRACT

The voltage applied to a first grid electrode 71 of an X-ray tube 11 by a grid voltage control section 110 is controlled with reference to a predetermined negative voltage from a negative voltage generating section 112 when an object 5 to be inspected does not exist in an imaging area (irradiation area of an X-ray from an X-ray source 1) so that the pulse outputted from a pulse generator 105 is in its OFF state, and is controlled with reference to a reference positive voltage from a reference voltage generating section 115 when the object 5 to be inspected exists in the imaging area in the X-ray image intensifier 2 (irradiation area of the X-ray from the X-ray source 1) so that the pulse outputted from the pulse generator 105 is in its ON state, whereby both of the cutoff voltage and grid operating voltage are applied in a stable state.

5 Claims, 4 Drawing Sheets

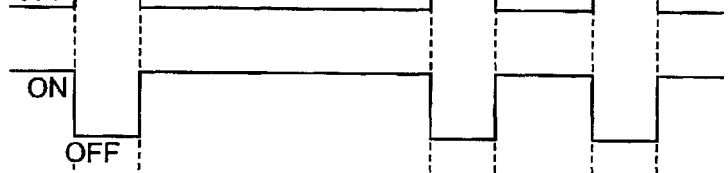
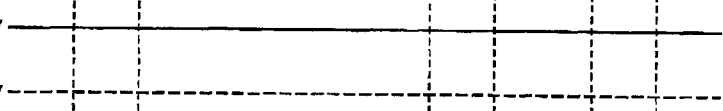
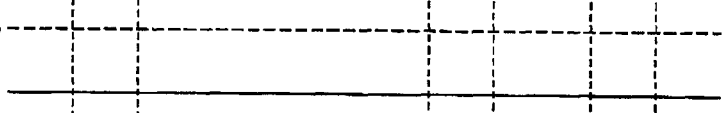
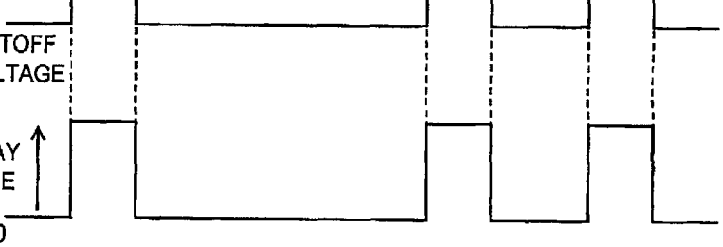

X-RAY GENERATING APPARATUS, X-RAY IMAGING APPARATUS, AND X-RAY INSPECTION SYSTEM

RELATED APPLICATION

This is a continuation-in-part application of application Ser. No. PCT/JP00/01238 filed on Mar. 2, 2000, now pending.

BACKGROUND OF THE INVENTION

1. Field of the Invention

The present invention relates to an X-ray generating apparatus for generating an X-ray by bombarding an anode target with an electron emitted from a cathode, an X-ray imaging apparatus for capturing an X-ray transmission image formed upon irradiating an object to be inspected with the X-ray generated by the X-ray generating apparatus, and an X-ray inspection system for inspecting the object to be inspected being transferred in a predetermined direction with an X-ray.

2. Related Background Art

Conventionally known as an X-ray generating apparatus having an X-ray tube for generating an X-ray by bombarding an anode target with an electron emitted from a cathode is one disclosed in U.S. Pat. No. 5,077,771. The X-ray generating apparatus disclosed in this publication uses a PWM system as a method of controlling the grid voltage applied to a grid electrode, so as to regulate the effective grid voltage by changing the pulse width of control pulses.

Typical inspecting apparatus often use a technique which captures an image (still image) of an object to be inspected by flashing (pulsing) a light source. While such a technique has been desired to be applied to X-ray inspections as well, examples realizing an X-ray generating apparatus adapted to pulse an X-ray generated from an X-ray tube have hardly been known. In an X-ray tube, the X-ray output generated therein will change greatly even if the voltage applied to each electrode changes only slightly. Therefore, stable pulsing X-rays are hard to generate, and a technique for generating stable pulsing X-rays has not fully be established yet.

SUMMARY OF THE INVENTION

In view of the points mentioned above, it is a first object of the present invention to provide an X-ray generating apparatus which can generate a stable pulsing X-ray from an X-ray tube.

It is a second object of the present invention to provide an X-ray imaging apparatus which can accurately acquire an X-ray transmission image formed upon irradiating an object to be inspected with a stable pulsing X-ray generated from an X-ray tube.

It is a third object of the present invention to provide an X-ray inspecting system which can irradiate an object to be inspected being transferred in a predetermined direction with a stable pulsing X-ray generated from an X-ray tube, thereby being able to accurately acquire an X-ray transmission image of the object formed upon irradiation with the stable pulsing X-ray.

For achieving the first object, the X-ray generating apparatus of the present invention comprises an X-ray tube for generating, within a housing sealed into vacuum, an X-ray by focusing an electron emitted from a cathode into an anode target by way of a first grid electrode, a second grid electrode, and a focusing electrode; grid voltage control means for controlling a grid voltage applied to the first grid electrode; and pulse generating means for generating a pulse which changes from an OFF state to an ON state and keeps the ON state for a predetermined period of time; wherein the grid voltage control means applies, in response to the pulse generated by the pulse generating means, a cutoff voltage to the first grid electrode when the pulse is in the OFF state so as to prevent the electron emitted from the cathode from reaching the anode target, and applies to the first grid electrode, in response to the pulse generated by the pulse generating means, a grid operating voltage adjusted such that the electron emitted from the cathode so as to bombard the anode target attains a predetermined amount of quantity when the pulse is in the ON state.

In response to the pulse generated by the pulse generating means, the grid voltage control means applies a cutoff voltage to the first grid electrode when the pulse is in the OFF state so as to prevent the electron emitted from the cathode from reaching the anode target, and applies to the first grid electrode a grid operating voltage adjusted such that the electron emitted from the cathode so as to bombard the anode target attains a predetermined value of quantity. As a consequence, the X-ray tube can generate a pulsing X-ray having a pulse width corresponding to the period during which the grid operating voltage is applied to the first grid electrode. Also, since the grid operating voltage applied to the first grid electrode is adjusted such that the electron emitted from the cathode so as to bombard the anode target attains a predetermined value of quantity, the pulsing X-ray generated from the X-ray tube can be stabilized.

The X-ray generating apparatus of the present invention may be characterized in that the grid voltage control means has cathode current detecting means for detecting a cathode current and, in response to the pulse generated by the pulse generating means, applies to the first grid electrode a grid operating voltage adjusted such that the cathode current detected by the cathode current detecting means attains a predetermined value when the pulse is in the ON state.

While the cathode current detecting means detects the cathode current, the grid voltage control means applies to the first grid electrode the grid operating voltage adjusted such that the cathode current attains a predetermined value. For example, means for detecting the anode target current may be provided as means for detecting the quantity of electron emitted to the cathode so as to bombard the anode target. However, a high voltage is usually applied to the anode target, whereby the anode target current is hard to detect. Hence, the cathode current detecting means can easily detect the quantity of the electron emitted from the cathode so as to bombard the anode target, whereby the grid voltage control means can easily adjust the grid operating voltage.

The X-ray generating apparatus of the present invention may be characterized in that the cathode current detecting means has a cathode current detecting resistor, connected to the cathode, for detecting the cathode current; and that the grid voltage control means has a negative voltage generating section for generating a predetermined negative voltage; a pulse inverter for inputting the pulse generated by the pulse generating means and generating an inverted pulse in which the ON and OFF states of the inputted pulse are inverted; a first switch for inputting the inverted pulse generated by the pulse inverter and outputting the predetermined negative voltage generated by the negative voltage generating section when the inverted pulse is in the ON state; a reference voltage generating section for generating a reference positive voltage; a second switch for inputting the pulse generated by the pulse generating means and outputting, when the pulse is in the ON state, the reference positive voltage generated by the reference voltage generating section; an operational amplifier having one input terminal for inputting a voltage generated by the cathode current detecting resistor and the other input terminal for inputting the predetermined negative voltage outputted from the first switch and the reference positive voltage outputted from the second switch; and a grid voltage control circuit for controlling, in response to an output from the operational amplifier, the grid voltage applied to the first grid electrode.

The configuration of the grid voltage control means for controlling the grid voltage applied to the first grid electrode in order to generate a stable pulsing X-ray can be realized by a simple, low-cost circuit configuration.

For achieving the second object, the X-ray imaging apparatus of the present invention comprises imaging means for capturing an X-ray transmission image formed upon irradiating an object to be inspected with the X-ray generated by the X-ray generating apparatus according to claim 1; wherein the imaging means receives the pulse generated by the pulse generating means and captures the X-ray transmission image when the pulse is in the ON state.

The imaging means receives the pulse generated by the pulse generating means, and captures the X-ray transmission image when the pulse is in the ON state. As a consequence, the imaging means can accurately acquire the X-ray transmission image formed upon irradiating the object to be inspected with the stable pulsing X-ray generated from the X-ray tube.

For achieving the third object, the X-ray inspection system of the present invention comprises the X-ray generating apparatus according to claim 1, an X-ray imaging apparatus having imaging means for capturing an X-ray transmission image formed upon irradiating an object to be inspected with an X-ray generated by the X-ray generating apparatus; and object detecting means for detecting arrival of the object in an imaging area in the X-ray imaging apparatus; wherein the pulse generating means has trigger signal outputting means for outputting a trigger signal according to the detection of the object by the object detecting means and outputs the pulse when the trigger signal is outputted from the trigger signal outputting means; and wherein the imaging means receives the pulse outputted from the pulse generating means and captures the X-ray transmission image when the pulse is in the ON state.

The arrival of the object to be inspected in the imaging area in the X-ray imaging apparatus is detected by the object detecting means and, according to the detection, the trigger signal generating means generates a trigger signal, and the pulse generating means generates a pulse. As a consequence, when the pulse is in the ON state, a stable pulsing X-ray is generated from the X-ray tube. In response to the pulse generated by the pulse generating means, the imaging means captures the X-ray transmission image when the pulse is in the ON state. Therefore, the object to be inspected being transferred in a predetermined direction can be irradiated with a stable pulsing X-ray, whereby the X-ray transmission image of the object formed upon irradiation with the stable pulsing X-ray can be acquired accurately.

For achieving the first object, the X-ray generating apparatus of the present invention comprises an X-ray tube having a cathode, an anode target, and a first grid electrode, a second grid electrode, and a focusing electrode which are disposed between the cathode and the anode target; and grid voltage control means for controlling a grid voltage applied to the first grid electrode such that a pulsing X-ray having a predetermined pulse width is generated from the X-ray tube.

The grid voltage control means controls the grid voltage applied to the first grid electrode such that a pulsing X-ray having a predetermined pulse width is generated from the ray tube. As a consequence, a pulsing X-ray having a predetermined pulse width can be generated from the X-ray tube.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 4A is a graph showing the change of an output signal from a photoelectric switch with time;

FIG. 4B is a graph showing the change of a trigger signal from a trigger signal generator with time;

FIG. 4C is a graph showing the change of an output pulse from a pulse generator with time;

FIG. 4D is a graph showing the change of a pulse fed into the second switch with time;

FIG. 4E is a graph showing the change of a pulse fed into the first switch with time;

FIG. 4F is a graph showing the change of target voltage with time;

FIG. 4G is a graph showing the change of cathode voltage with time;

FIG. 4H is a graph showing the change of a voltage from the first grid electrode power supply section with time;

FIG. 4I is a graph showing the change of a voltage applied to the first grid electrode with time; and FIG. 4J is a graph showing the change of the X-ray output with time.

DESCRIPTION OF THE PREFERRED EMBODIMENTS

The X-ray inspection system in accordance with an embodiment of the present invention will be explained with reference to the drawings. The X-ray generating apparatus and X-ray imaging apparatus in accordance with embodiments of the present invention are included in the X-ray inspection system in accordance with this embodiment.

Figure 1:
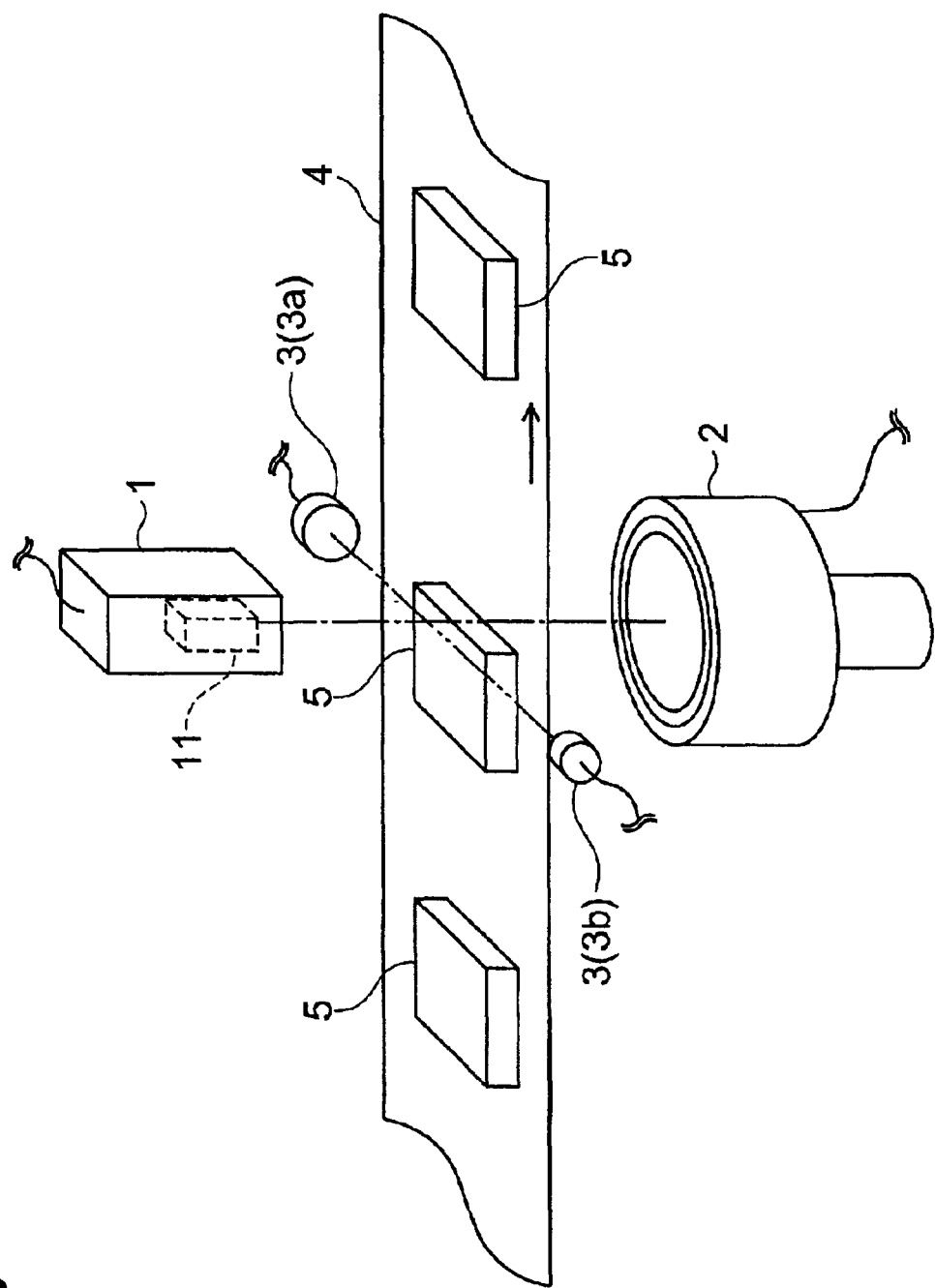
FIG. 1 is a perspective view showing an X-ray inspection system.

First, the arrangement of an X-ray source 1, an X-ray image intensifier 2 as imaging means, and a photoelectric switch 3 in the X-ray inspection system in accordance with this embodiment will be explained. FIG. 1 is a perspective view showing the X-ray inspection system in accordance with this embodiment.

A belt conveyor 4 moves in the direction indicated by the arrow in the drawing. Objects 5 to be inspected are placed on the belt conveyor 4 and are transferred in the direction indicated by the depicted arrow as the belt conveyor 4 moves. The X-ray source 1 is arranged above the belt conveyor 4, and divergently outputs an X-ray from an X-ray tube 11 into a predetermined angular range, whereby, among the objects 5 on the belt conveyor 4, those located within a predetermined area are irradiated with the X-ray. While opposing the X-ray source 1 with the belt conveyor 4 inserted therebetween, the X-ray image intensifier 2 is disposed at a position where the X-ray outputted from the X-ray source 1 (X-ray tube 11) can reach, and captures X-ray transmission images of the objects 5 according to the gate signal fed therein.

Disposed laterally to the belt conveyor 4 is the photoelectric switch 3 as means for detecting the arrival of the objects 5 in the imaging area in the X-ray image intensifier 2 (the irradiation area of the X-ray from the X-ray source 1). The photoelectric switch 3 has a light-emitting device 3a and a light-receiving device 3b which oppose each other across the belt conveyor 4. The passage of the objects 5 is detected by utilizing the fact that light from the light-emitting device 3a is blocked when the objects 5 reach the position on the belt conveyor 4 where the photoelectric switch 3 is disposed. In the state where no objects 5 exist, the light from the light-emitting device 3a is not blocked, whereby the output signal from the photoelectric switch 3 (light-receiving device 3b) attains its ON state. When the objects 5 reach the position where the photoelectric switch 3 is disposed, the light from the light-emitting device 3a is blocked, whereby the output signal from the photoelectric switch 3 (light-receiving device 3b) attains its OFF state.

Figure 2:
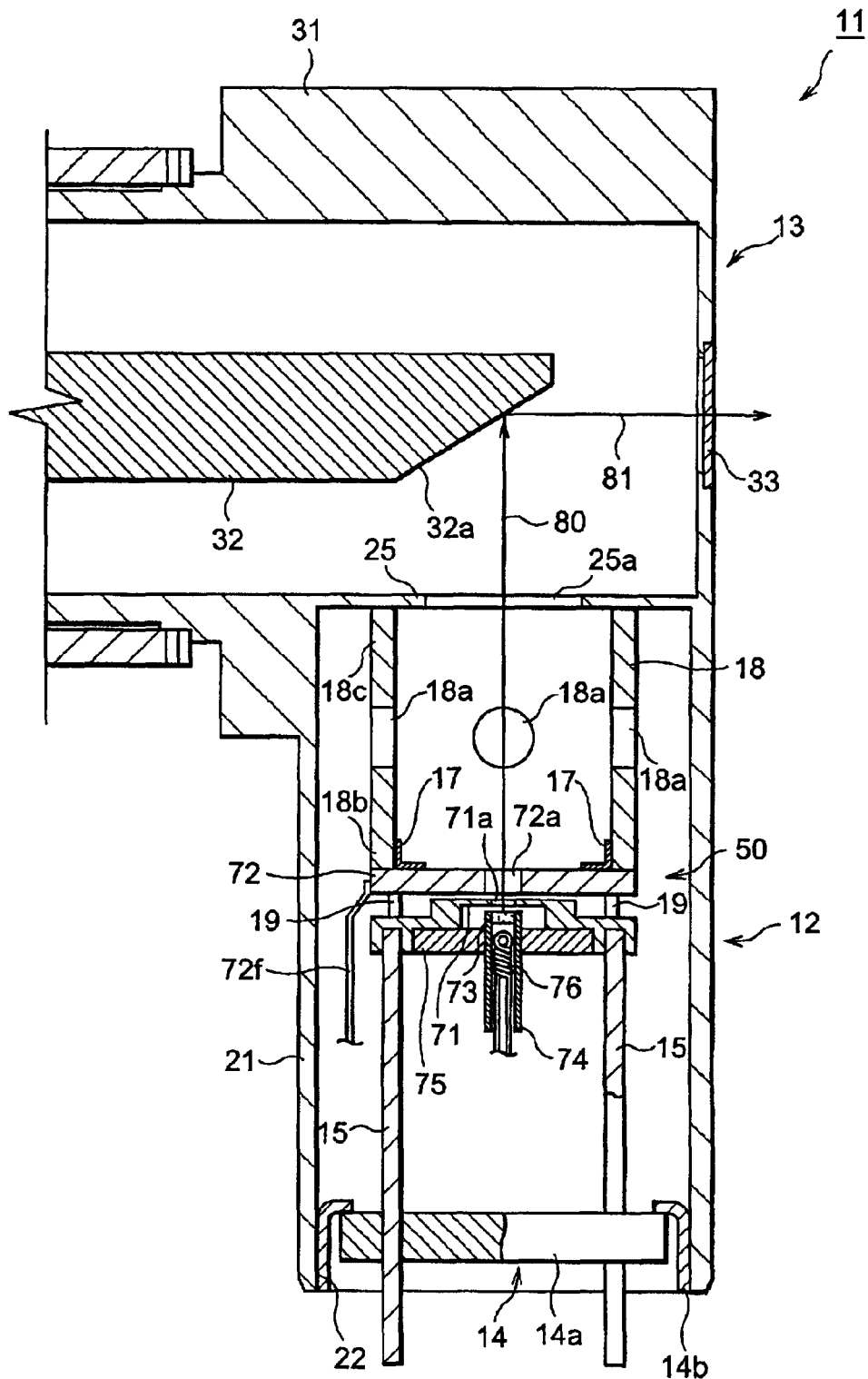
FIG. 2 is a sectional view showing a main part of an X-ray tube included in the X-ray inspection system.

The X-ray source 1 has the X-ray tube 11 shown in FIG. 2. FIG. 2 is a sectional view showing a main part of the X-ray tube included in the X-ray inspection system in accordance with this embodiment. The X-ray tube 11 is a microfocus X-ray tube; and comprises an electron gun section 12 for generating and emitting an electron 80, and an X-ray generating section 13 for receiving the electron 80 from the electron gun section 12 and generating an X-ray 81. The respective shells of the electron gun section 12 and X-ray generating section 13 are constituted by tubular containers 21, 31 acting as housings for accommodating individual constituents. The containers 21, 31 are each made of an electric conductor and are connected to each other so as to be orthogonal to each other. The containers 21, 31 are partitioned from each other with a focusing electrode 25 formed at the boundary portion between the containers 21, 31, but are communicated to each other through an opening 25a formed in the focusing electrode 25. An electron gun 50 and an anode target 32 are arranged within the containers 21, 31, respectively. Also, each of the containers 21, 31 is sealed hermetically, so as to attain a vacuum state therein.

Schematically, the electron gun 50 arranged within the container 21 comprises a heater 76 as a heat source; a cathode 73 as a thermoelectron source for generating and emitting the electron 80 upon heating with the heater 76; first and second grid electrodes 71, 72 for accelerating and focusing the electron 80 emitted from the cathode 73; a spacer 18, disposed between the second grid electrode 72 and the focusing electrode 25, for setting the gap between the second grid electrode 72 and the focusing electrode 25 to a predetermined distance; a plurality of pins 15 for supplying a predetermined voltage to the first and second grid electrodes 71, 72, heater 76, and cathode 73 from the outside of the container; and a stem 14 functioning as a lid portion of the container while securing the pins 15 penetrating therethrough.

The stem 14, heater 76, cathode 73, first and second grid electrodes 71, 72, and spacer 18 are arranged in parallel in this order toward the focusing electrode 25, such that the respective axial centers of these constituents align with each other and are positioned coaxial with the axial center of the opening 25a of the focusing electrode 25 and the axial center of the container 21 having a tubular form. The first and second grid electrodes 71, 72 are disposed between the cathode 73 and the anode target 32. Further in detail, the cathode 73 is provided at the front end of a tubular body 74 made of an insulator, whereas the heater 76 for heating the cathode 73 is provided within the tubular body 74. The first grid electrode 71 is disposed on the focusing electrode 25 side of the cathode 73, whereas the second grid electrode 72 is disposed on the focusing electrode 25 side of the first grid electrode 71. The second grid electrode 72 is supported by way of a plurality of ceramic rods (insulators) 19 on the focusing electrode 25 side of the first grid electrode 71, whereas the tubular body 74 having the cathode 73 and heater 76 is supported by way of an insulator 75 on the side of the first grid electrode 71 opposite the focusing electrode 25.

The first and second grid electrodes 71, 72, each shaped like a disk, have openings 71a, 72a, respectively, through which the electron 80 from the cathode 73 passes. The second grid electrode 72 is an electrode for pulling the electron 80 from the cathode 73 toward the target 32 within the container 31. The first grid electrode 71 is an electrode for pushing the electron 80, which is pulled by the second grid electrode 72 toward the target 32, back toward the cathode 73. When the voltage supplied to the first grid electrode 71 is adjusted, the electron 80 directed toward the target 32 is enhanced or lowered. Also, the openings 71a, 72a of the first and second grid electrodes 71, 72 constitute a minute electron lens group for focusing the electron from the cathode 73 onto the target 32.

The spacer 18 is disposed between the second grid electrode 72 and the focusing electrode 25. The spacer 18 is shaped like a tube such that the electron 80 directed from the cathode 73 to the target 32 can pass there through, and has a predetermined length in the axial direction. Its end part 18b on one side is secured to the end face of the second grid electrode 72, whereas the end part 18c on the other side abuts against the focusing electrode 25. Since the spacer 18 having a predetermined length is disposed between the second grid electrode 72 and the focusing electrode 25, the gap between the second grid electrode 72 and focusing electrode 25 is set to a predetermined distance. The predetermined distance mentioned here is the distance between the second grid electrode 72 and focusing electrode 25 required for yielding a desirable focal diameter. The spacer 18 is made of an electric conductor such as stainless steel, for example, whereas the second grid electrode 72 for securing the spacer 18 is made of Mo (molybdenum) having a favorable heat resistance, for example. Since Mo, which is hard to weld in a usual manner, is thus used as the second grid electrode 72, a plurality of Ni (nickel) ribbons 17 are used so as to connect the second grid electrode 72 and the spacer 18 to each other by resistance welding. The connection by use of the Ni ribbons 17 is effected between the end face of the second grid electrode 72 and the inner peripheral face of the end part 18b on one side of the spacer 18. The spacer 18 has a peripheral wall formed with a plurality of venting holes 18a for communicating the space portion on the target 32 side and the space portion on the cathode 73 side, which are defined by boundaries formed by the spacer 18 and the second grid electrode 72 for securing the spacer 18, to each other.

The first grid electrode 71 has a plurality of pins 15 provided on the side thereof opposite the target 32. These pins 15 penetrate through a disk-shaped stem substrate 14a, which is made of an insulator such as ceramics, for example, and are secured to the stem substrate 14a. Namely, the first grid electrode 71 supporting the spacer 18, second grid electrode 72, tubular body 74, and the like is supported by the stem substrate 14a by way of a plurality of pins 15. A plurality of other pins, which are not depicted, also penetrate through the stem substrate 14a and are secured thereby. Connected to the plurality of other pins are a lead 72f of the second grid electrode 72, and leads of the cathode 73 and heater 76 which are not depicted. Also, an annular stem ring 14b is joined to the outer periphery of the stem substrate 14a.

The electron gun 50 is configured as in the foregoing. By brazing or the like, for example, the stem ring 14b of the electron gun 50 is firmly attached to an opening portion 22 formed at an end part of the container 21. Since the stem ring 14b is firmly attached to the opening portion 22 of the container 21, the opening portion 22 is closed with the stem 14 constituted by the stem substrate 14a and stem ring 14b, whereby the containers 21, 31 are sealed hermetically.

As shown in FIG. 2, the target 32 is installed within the container 31 communicating with the container 21 by way of the opening 25a of the focusing electrode 25. The target 32 receives the electron 80 from the electron gun 80 and generates the X-ray 81. It is a rod-like body made of a metal and is arranged such that its axial direction intersects the advancing direction of the electron 80. The front end face 32a of the target 32 is a face for receiving the electron 80 from the electron gun 50, and is disposed at a position in front of the advancing electron 80 and formed into an inclined surface such that the incoming electron 80 and the outgoing X-ray 81 are orthogonal to each other. The container 31 is formed with an X-ray exit window 33. The X-ray exit window 33 is a window for causing the X-ray 81 emitted from the target 32 to exit to the outside of the container 31, and is constituted by a sheet member made of Be material, which is a material transparent to X-rays, for example. The X-ray exit window 33 is disposed in front of the front end of the target 32, and is formed such that its center is positioned on the extension of the center axis of the target 32.

Figure 3:
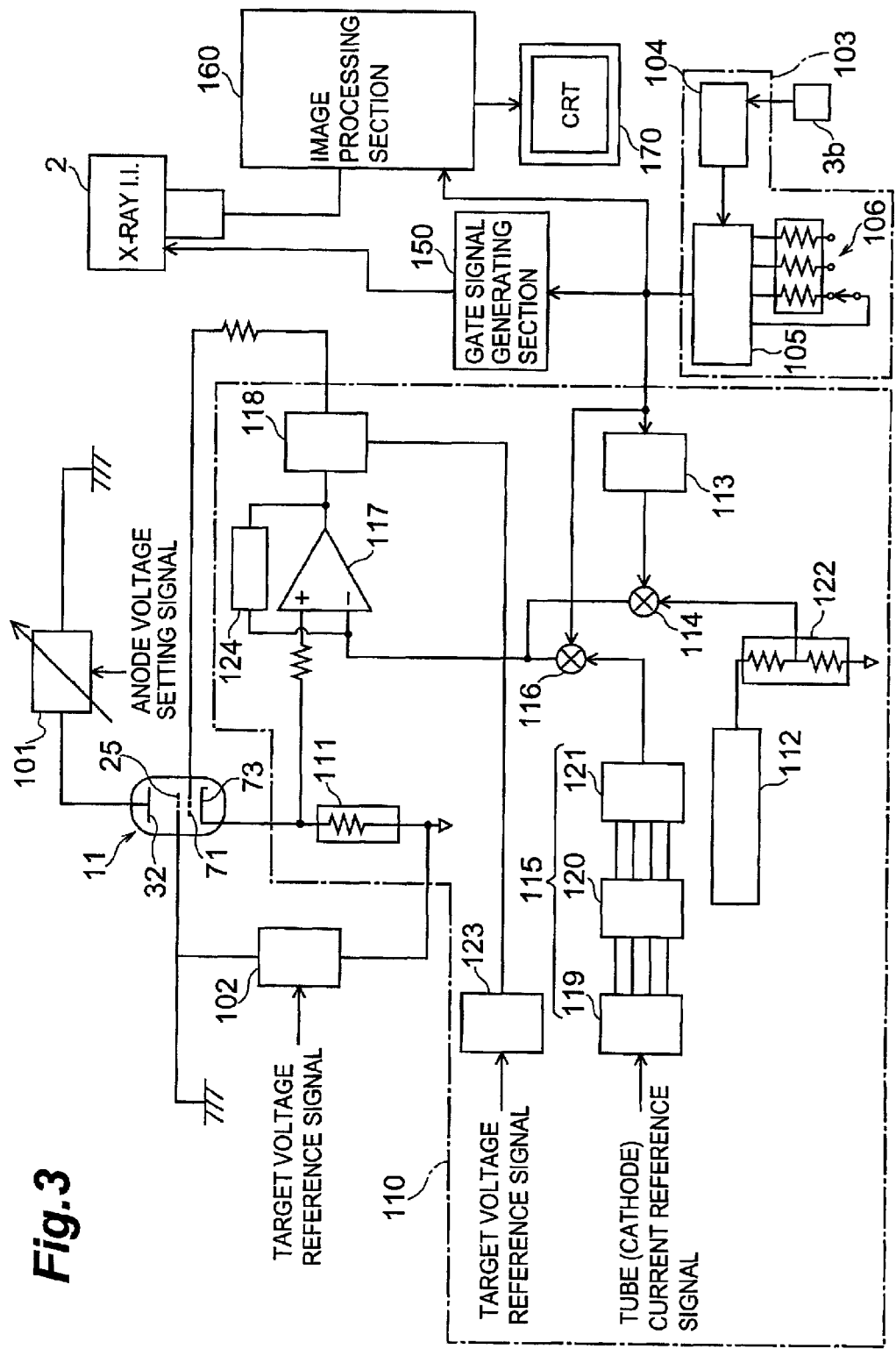
FIG. 3 is a block diagram showing the configuration of the X-ray inspection system.

FIG. 3 is a block diagram showing the configuration of the X-ray inspection system in accordance with this embodiment. This X-ray inspection system comprises not only the X-ray tube 11 (X-ray source 1), X-ray image intensifier 2, and photoelectric switch 3 (light-receiving device 3b) mentioned above, but also a target power supply section 101, a cathode power supply section 102, a pulse generating section 103 as pulse generating means, a grid voltage control section 110 as grid voltage control means, a gate signal generating section 150, an image processing section 160, and a CRT 170. In FIG. 3, the X-ray tube 11 is depicted in a simplified manner omitting the second grid electrode 72, the heater 76, and the like.

The target power supply section 101 applies a predetermined positive high voltage (target voltage) to the target 32. The cathode power supply section 102 applies a predetermined voltage (cathode voltage) to the cathode 73. According to the signal outputted from the light-receiving device 3b, the pulse generating section 103 generates a pulse whose ON state is kept for a predetermined period of time. The grid voltage control section 110 controls the voltage applied to the first grid electrode 71. According to the pulse outputted from the pulse generating section 103, the gate signal generating section 150 generates a gate signal, and supplies this gate signal to the X-ray image intensifier 2. An X-ray transmission image of the object 5 to be inspected is fed to the image processing section 160, and is subjected to image processing (image enlargement and the like) therein. The image data from the image processing section 160 is fed to the CRT 170, whereby the latter displays the X-ray transmission image subjected to image processing in the image processing section 160.

An anode voltage setting signal is fed into the target power supply section 101 from a control unit which is not depicted. The target power supply section 101 generates a predetermined high voltage (target voltage) corresponding to the anode voltage setting signal. A target reference signal indicative of the target voltage detected by the target voltage detecting section is fed into the cathode power supply section 102 from a target voltage detecting section which is not depicted. The cathode power supply section 102 generates a predetermined voltage (cathode voltage) corresponding to the target voltage reference signal.

The pulse generating section 103 comprises a trigger signal generator 104 for inputting a signal outputted from the light-receiving device 3b, and a pulse generator 105 for inputting a trigger signal outputted from the trigger signal generator 104. At the time when the signal outputted from the light-receiving device 3b changes from the ON state to the OFF state, the trigger signal generator 104 generates a trigger signal having a predetermined pulse width and outputs thus generated trigger signal. At the time when the trigger signal is inputted, the pulse generator 105 generates a pulse whose ON state is kept for a predetermined period of time, and outputs thus generated pulse. The pulse generating section 103 further comprises a timer 106 for variably setting the above-mentioned predetermined period of time during which the ON state of the pulse outputted to the pulse generator 105 is kept.

The grid voltage control section 110 is provided between the cathode power supply section 102 and the cathode 73. The grid voltage control section 110 comprises a cathode current detecting resistor 111 as cathode current detecting means, a negative voltage generating section 112, a pulse inverter 113 for inputting the pulse from the pulse generator 105, a first switch 114 for inputting an inverted pulse from the pulse inverter 113, a second switch 116 for inputting the pulse from the pulse generator 105, an operational amplifier 117, and a grid voltage control circuit 118.

The cathode current detecting resistor 111 detects the cathode current. The negative voltage generating section 112 generates a predetermined negative voltage. The pulse inverter 113 generates an inverted pulse in which the ON and OFF states of the inputted pulse are inverted. At the time when the inverted pulse from the pulse inverter 113 is in the ON state, the first switch 114 outputs the predetermined negative voltage generated by the negative voltage generating section 112. A reference voltage generating section 115 generates a reference positive voltage. At the time when the pulse from the pulse generator 105 is in the ON state, the second switch 116 outputs the reference positive voltage generated by the reference voltage generating section 115. The operational amplifier 117 has an input terminal (+) and an input terminal (−). The voltage generated by the cathode current detecting resistor 111 is fed to the input terminal (+), whereas the predetermined negative voltage outputted from first switch 114 or the reference positive voltage outputted from second switch 116 is fed to the input terminal (−). The grid voltage control circuit 118 receives the output from the operational amplifier 117 and controls the voltage applied to the first grid electrode 71.

The reference voltage generating section 115 has an A/D converter 119 for inputting a tube (cathode) current reference signal outputted from the control unit, which is not depicted, or the like and converting the tube (cathode) current reference signal into a predetermined digital signal; a photocoupler 120 for inputting the output signal from the A/D converter 119; and a D/A converter 121 for converting the output signal from the photocoupler 120 into a predetermined analog signal. The output signal finally outputted from the D/A converter 121 corresponds to a signal indicative of the above-mentioned reference positive voltage. Also, a voltage divider 122 is provided between the negative voltage generating section 112 and the first switch 114, whereby the predetermined negative voltage supplied from the negative voltage generating section 112 is divided by the voltage divider 122, and the resulting partial voltage is supplied to the first switch 114.

Supplied to the grid voltage control circuit 118 is a voltage from a first grid electrode power supply section 123 for generating the voltage to be applied to the first grid electrode 71. According to the output from the operational amplifier 117, the grid voltage control circuit 118 controls the voltage supplied from the first grid electrode power supply section 123, so as to apply to the first grid electrode 71 a cutoff voltage such that the electron emitted from the cathode 73 does not reach the target 32, or a grid operating voltage such that the electron emitted from the cathode 73 bombards the target 32.

The target voltage reference signal indicative of the target voltage detected by the target voltage detecting section is fed from the target voltage detecting section, which is not depicted, into the first grid electrode power supply section 123 as in the cathode power supply section 102. The first grid electrode power supply section 123 generates a predetermined voltage (grid voltage) corresponding to the target voltage reference signal.

In this embodiment, a clamping circuit 124 for connecting an upstream position of the input terminal (−) of the operational amplifier 117 and a downstream position of the operational amplifier 117 to each other is provided, so as to maintain the stable state of the operational amplifier 117 when no trigger signal is inputted (in the OFF state). Since the clamping circuit 124 is inserted at this position, the operational amplifier 117 can output a current pulse with a faster rising time when the reference voltage from the reference voltage generating section 115 is fed to the input terminal (−) of the operational amplifier 117 upon generation of a pulse from the pulse generator 105.

Operations of the X-ray inspection system in accordance with this embodiment will now be explained with reference to FIGS. 4A to 4J.

As shown in FIG. 4F, a predetermined high voltage (+HV) is supplied as a target voltage from the target power supply section 101 to the target 32. As shown in FIG. 4G, a predetermined voltage (V1) is supplied as a cathode voltage from the cathode power supply section 102 to the cathode 73. As shown in FIG. 4H, a predetermined voltage (V2<V1) is supplied from the first grid electrode power supply section 123 to the grid voltage control circuit 118.

When the object 5 to be inspected mounted on the belt conveyor 4 enters the imaging area in the X-ray image intensifier 2 (the irradiation area of the X-ray from the X-ray source 1) as being transferred in the direction of arrow in FIG. 1, the object 5 crosses the line connecting the light-emitting device 3a and light-receiving device 3b of the photoelectric switch 3, whereby the light emitted from the light-emitting device 3a is blocked by the object 5. When the light emitted from the light-emitting device 3a is blocked by the object 5, the output signal from the light-receiving device 3b attains the OFF state as shown in FIG. 4A. When the object 5 does not exist within the imaging area in the X-ray image intensifier 2 (the irradiation area of the X-ray from the X-ray source 1), the light emitted from the light-receiving device 3a is not blocked by the object 5, whereby the output signal from the light-receiving device 3b attains the ON state as shown in FIG. 4A.

The output signal from the light-receiving device 3b is fed into the trigger signal generator 104, whereby the trigger signal generator 104 detects a change of the output signal from the light-receiving device 3b from the ON state to the OFF state (falling of the output signal). In synchronization with thus detected change from the ON state to the OFF state (falling of the output signal), the trigger signal generator 104 outputs a trigger signal as shown in FIG. 4B. The trigger signal outputted from the trigger signal generator 104 is fed into the pulse generator 105. The pulse generator 105 detects the input of the trigger signal, the rising of the trigger signal in particular, and outputs a pulse whose ON state is kept for a predetermined period of time (pulse width a) corresponding to the time set by the timer 106 as shown in FIG. 4C.

The pulse outputted from the pulse generator 105 is fed into the pulse inverter 113, second switch 116, gate signal generating section 150, and image processing section 160. As shown in FIG. 4E, the pulse inverter 113 outputs to the first switch 114 an inverted pulse in which the ON and OFF states of the inputted pulse are inverted. The first switch 114 operates such that a predetermined negative voltage (partial voltage) supplied from the negative voltage generating section 112 by way of the voltage divider 122 is fed to the negative input terminal of the operational amplifier 117 when the inverted pulse is in the ON state. Also, the first switch 114 operates such that the predetermined negative voltage (partial voltage) from the negative voltage generating section 112 is not fed to the negative input terminal of the operational amplifier 117 when the inverted pulse is in the OFF state.

As shown in FIG. 4D, the pulse from the pulse generator 105 is fed into the second switch 116. The second switch 116 operates such that the reference positive voltage supplied from the reference voltage generating section 115 is not fed to the input terminal (−) of the operational amplifier 117 when the inputted pulse is in the OFF state. Also, the second switch 116 operates such that the reference positive voltage supplied from the reference voltage generating section 115 is fed to the input terminal (−) of the operational amplifier 117 when the inputted pulse is in the ON state. Therefore, the predetermined negative voltage (partial voltage) supplied from the negative voltage generating section 112 by way of the voltage divider 122 is fed to the input terminal (−) of the operational amplifier 117 when the pulse outputted from the pulse generator 105 is in the OFF state, whereas the reference positive voltage supplied from the reference voltage generating section 115 is similarly fed to the input terminal (−) of the operational amplifier 117 when the pulse outputted from the pulse generator 105 is in the ON state.

The voltage generated by the cathode current detecting resistor 111 is supplied to the input terminal (+) of the operational amplifier 117. The operational amplifier 117 is configured so as to output a signal such that the input to the input terminal (+) and the input to the input terminal (−) are at the same potential with reference to the input to the input terminal (−). When the pulse outputted from the pulse generator 105 is in the OFF state so that the predetermined negative voltage (partial voltage) supplied from the negative voltage generating section 112 by way of the voltage divider 122 is fed to the input terminal (−) of the operational amplifier 117, the operational amplifier 117 outputs a signal such that the voltage generated by the cathode current detecting resistor 111 is at the same potential as the predetermined negative voltage (partial voltage) from the negative voltage generating section 112.

The output from the operational amplifier 117 is sent to the grid voltage control circuit 118, so that a predetermined voltage (V2) from the first grid electrode power supply section 123 is controlled, whereby a cutoff voltage (negative) for preventing the electron emitted from the cathode 73 from reaching the target 32 is provided as shown in FIG. 4I. As a consequence, the electron emitted from the cathode 73 does not reach the target 32, whereby no X-ray is generated from the X-ray tube 11 as shown in FIG. 4J. Since the electron emitted from the cathode 73 does not reach the target 32, no cathode (tube) current occurs, whereby the voltage occurring in the cathode current detecting resistor 111 becomes zero. The voltage sent to the input terminal (+) of the operational amplifier 117 becomes zero, whereas the predetermined negative voltage (partial voltage) from the negative voltage generating section 112 is continuously supplied to the input terminal (−) of the operational amplifier 117, whereby the output of the operational amplifier 117 allows the grid voltage control circuit 118 to supply a stable cutoff voltage (negative) to the first grid electrode 71.

When the pulse outputted from the pulse generator 105 is in the ON state so that the reference positive voltage supplied from the reference voltage generating section 115 is fed to the input terminal (−) of the operational amplifier 117, the operational amplifier 117 outputs a signal such that the voltage generated by the cathode current detecting resistor 111 attains the same potential as the reference positive voltage.

The output from the operational amplifier 117 is sent to the grid voltage control circuit 118, so that the predetermined voltage (V2) from the first grid electrode power supply section 123 is controlled, whereby a grid operating voltage (positive) for causing the electron emitted from the cathode 73 to bombard the target 32 is supplied to the first grid electrode 71 as shown in FIG. 4I. As a result, the electron emitted from the cathode 73 bombards the target 32, so that a pulsing X-ray having a pulse width equivalent to the period of time (pulse width a) during which the ON state of the pulse generated by the pulse generator 105 is maintained is generated from the X-ray tube 11 as shown in FIG. 4J, where by the object 5 is irradiated with this pulsing X-ray. Here, the electron emitted from the cathode 73 bombards the target 32, so that a cathode (tube) current occurs, whereby a predetermined voltage occurs in the cathode current detecting resistor 111 due to a voltage drop. The predetermined voltage is sent to the input terminal (+) of the operational amplifier 11, whereas the reference positive voltage is continuously fed to the input terminal (−) of the operational amplifier 117, thus carrying out so-called feedback control of the grid operating voltage applied to the first grid electrode 71, in which the output from the operational amplifier 117 to the grid voltage control circuit 118 is effected such that the predetermined voltage sent to the input terminal (+) of the operational amplifier 117 is at the same potential as the reference positive voltage. As a consequence, the grid voltage control circuit 118 supplies a stable grid operating voltage to the first grid electrode 71.

The pulse outputted from the pulse generator 105 is also fed into the gate signal generating section 150 and image processing section 160 as mentioned above. The gate signal generating section 150 outputs a gate signal in synchronization with the inputted pulse. According to the inputted gate signal, the X-ray image intensifier 2 captures the X-ray transmission image formed upon irradiating the object 5 with the X-ray from the X-ray source 1 (X-ray tube 11). In synchronization with the inputted pulse, the image processing section 160 stores data of the X-ray transmission image of the object 5 captured by the X-ray image intensifier 2 into a frame memory (not depicted). Thereafter, the image processing section 160 carries out a predetermined image processing operation (image enlargement or the like) for the data of the X-ray transmission image of the object 5 stored in the frame memory, and outputs the image data of the X-ray transmission image of the object 5 after the image processing to the CRT 170. The X-ray transmission image of the object 5 after the image processing is displayed on the CRT 170. The X-ray transmission image stored in the frame memory can be seen as a still image of the object 5 at the timing when the gate signal is generated (the pulse is outputted from the pulse generator 105).

First, in the above-mentioned X-ray inspection system of this embodiment, the voltage applied to the first grid electrode 71 by the grid voltage control section 110 is controlled with reference to a predetermined negative voltage (partial voltage) from the negative voltage generating section 112 when the object 5 to be inspected does not exist in the imaging area in the X-ray image intensifier 2 (the irradiation area of the X-ray from the X-ray source 1) (when the pulse outputted from the pulse generator 105 is in the OFF state). On the other hand, it is controlled with reference to the reference positive voltage from the reference voltage generating section 115 when the object 5 exists within the imaging area in the X-ray image intensifier 2 (the irradiation area of the X-ray from the X-ray source 1) (when the pulse outputted from the pulse generator 105 is in the ON state). As a consequence, both of the cutoff voltage and grid operating voltage are applied in a stable state.

Further, in response to changes in the pulse (from the ON state to the OFF state or from the OFF state to the ON state) from the pulse generator 105, the first switch 114 and second switch 116 operate quickly, whereby one of the predetermined negative voltage (partial voltage) and the reference positive voltage from the reference voltage generating section 115 is immediately supplied to the input terminal (−) of the operational amplifier 117 in a selective manner. Therefore, the voltage applied from the grid voltage control circuit 118 to the first grid electrode 71 rapidly changes from the cutoff voltage to the grid operating voltage (the rising in FIG. 4I) or from the grid operating voltage to the cutoff voltage (the falling in FIG. 4I).

In view of the foregoing, a pulsing X-ray corresponding to the period of time (pulse width a) during which the pulse generated by the pulse generator 105 is kept in the ON state can be generated in a stabilized state from the X-ray tube 11.

Since the cathode current detecting resistor 111 is provided as means for detecting the quantity of electron emitted from the cathode 73 so as to bombard the target 32, and the cathode current is detected thereby, electron emitted from the cathode 73 so as to bombard the target 32 can be detected easily as compared with those provided with means for detecting the target current and the like, and the grid voltage control section 110 (grid voltage control circuit 118) can easily control the voltage applied to the first grid electrode 71.

Further, the configuration of the grid voltage controlling section 110 for controlling the voltage applied to the first grid electrode 71 in order to generate a stable pulsing X-ray is effective in that it can be realized by a simple, low-cost circuit configuration.

According to the gate signal outputted from the gate signal generating section 150 in response to the pulse generated by the pulse generator 105, the X-ray image intensifier 2 captures the X-ray transmission image formed upon irradiating the object 5 with X-rays from the X-ray source 1 (X-ray tube 11) when the gate signal is outputted (when the pulse is in the ON state). Therefore, the X-ray image intensifier 2 can accurately acquire the X-ray transmission image formed upon irradiating the object 5 with the stable pulsing X-ray generated from the X-ray source 1 (X-ray tube 11).

The arrival of the object 5 in the imaging area in the X-ray image intensifier 2 (the irradiation area of the X-ray from the X-ray source 1) is detected by the photoelectric switch 3. According to this detection, the trigger signal generator 104 generates a trigger signal, whereby the pulse generator 105 generates a pulse. Consequently, as mentioned above, a stable pulsing X-ray is generated from the X-ray tube 11 when the pulse is in the ON state. Also, according to the gate signal outputted from the gate signal generating section 150 in response to the pulse generated by the pulse generator 105, the X-ray image intensifier 2 captures the X-ray transmission image formed upon irradiating the object 5 with the X-ray from the X-ray source 1 (X-ray tube 11) when the gate signal is outputted (when the pulse generated by the pulse generator 105 is in the ON state). Consequently, the object 5 mounted on the belt conveyor 4 being transferred can be irradiated with a stable pulsing X-ray generated from the X-ray tube 11, and the X-ray image intensifier 2 can accurately acquire the X-ray transmission image of the object formed upon irradiation with the stable pulsing X-ray.

When the tube (cathode) current reference signal fed into the reference voltage generating section 115 is configured such that it can be set variable, the reference positive voltage outputted from the reference voltage generating section 115 changes in response to the tube (cathode) current reference signal that is made variable. As a consequence, the reference value in the operational amplifier 117 changes, so that the voltage value of the grid operating voltage applied from the grid voltage control circuit 118 to the first grid electrode 71 is altered, which modifies the quantity of electron emitted from the cathode 73 so as to bombard the target 32, whereby the X-ray dose generated in the X-ray tube 11 can be changed. A stable pulsing X-ray can also be generated in this case as a matter of course.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An X-ray generating apparatus comprising:
    an X-ray tube for generating, within a housing sealed into vacuum, an X-ray by focusing an electron emitted from a cathode into an anode target by way of a first grid electrode, a second grid electrode, and a focusing electrode;
    grid voltage control means for controlling a grid voltage applied to said first grid electrode; and
    pulse generating means for generating a pulse which changes from an OFF state to an ON state and maintains said ON state for a predetermined period of time;
    wherein said first grid electrode is disposed on the focusing electrode side of said cathode, whereas said second grid electrode is disposed on the focusing electrode side of said first grid electrode;
    wherein said grid voltage control means has cathode current detecting means for detecting a cathode current and, in response to said pulse generated by said pulse generating means, applies a cutoff voltage to said first grid electrode when said pulse is in said OFF state so as to prevent said electron emitted from said cathode from reaching said anode target, and applies to said first grid electrode, in response to said pulse generated by said pulse generating means, a grid operating voltage adjusted such that said cathode current detected by said cathode current detecting means attains a predetermined value when said pulse is in said ON state;
    wherein said cathode current detecting means has a cathode current detecting resistor, connected to said cathode, for detecting said cathode current; and
    wherein said grid voltage control means has:
        an operational amplifier having one input terminal for inputting a voltage generated by said cathode current detecting resistor and the other input terminal for inputting a predetermined negative voltage or a reference voltage positive voltage; and
        a grid voltage control circuit for controlling, in response to an output from said operational amplifier, said grid voltage applied to said first grid electrode.

2. The X-ray generating apparatus according to claim 1, wherein said predetermined negative voltage is fed to the other input terminal of said operational amplifier and said operational amplifier outputs a signal such that said voltage generated by said cathode current detecting resistor is at the same potential as said predetermined negative voltage when said pulse outputted from said pulse generating means is in the OFF state, whereas said reference positive voltage is fed to the other input terminal of said operational amplifier and said operational amplifier outputs a signal such that said voltage generated by said cathode current detecting resistor attains the same potential as said reference positive voltage when said pulse outputted from said pulse generating mean is in the ON state.

3. The X-ray generating apparatus according to claim 1, wherein said grid voltage control means has further:
    a negative voltage generating section for generating said predetermined negative voltage;
    a pulse inverter for inputting said pulse generated by said pulse generating means and generating an inverted pulse in which said ON and OFF states of said inputted pulse are inverted;
    a first switch for inputting said pulse generated by said pulse inverter and outputting, when said inverted pulse is in said ON state, said predetermined negative voltage generated by said negative voltage generating section;
    a reference voltage generating section for generating said reference positive voltage; and
    a second switch for inputting said pulse generated by said pulse generating means and outputting, when said pulse is in said ON state, said reference positive voltage generated by said reference voltage generating section;

wherein said predetermined negative voltage outputted from said first switch or said reference positive voltage outputted from said second switch is fed to the other input terminal of said operational amplifier.

4. An X-ray imaging apparatus comprising imaging means for capturing an X-ray transmission image formed upon irradiating an object to be inspected with an X-ray generated by an X-ray generating apparatus;

wherein said X-ray generating apparatus comprises:
an X-ray tube for generating, within a housing sealed into vacuum, an X-ray by focusing an electron emitted from a cathode into an anode target by way of a first grid electrode, a second grid electrode, and a focusing electrode;
grid voltage control means for controlling a grid voltage applied to said first grid electrode; and
pulse generating means for generating a pulse which changes from an OFF state to an ON state and maintains said ON state for a predetermined period of time;

wherein said grid voltage control means has cathode current detecting means for detecting a cathode current and, in response to said pulse generated by said pulse generating means, applies a cutoff voltage to said first grid electrode when said pulse is in said OFF state so as to prevent said electron emitted from said cathode from reaching said anode target, and applies to said first grid electrode, in response to said pulse generated by said pulse generating means, a grid operating voltage adjusted such that said cathode current detected by said cathode current detecting means attains a predetermined value when said pulse is in said ON state; and wherein said cathode current detecting means has a cathode current detecting resistor, connected to said cathode, for detecting said cathode current;

wherein said grid voltage control means has:
an operational amplifier having one input terminal for inputting a voltage generated by said cathode current detecting resistor and the other input terminal for inputting a predetermined negative voltage or a reference positive voltage; and
a grid voltage control circuit for controlling, in response to an output from said operational amplifier, said grid voltage applied to said first grid electrode; and wherein said imaging means receives said pulse generated by said pulse generating means and captures said X-ray transmission image when said pulse is in said ON state.

5. An X-ray inspection system comprising an X-ray generating apparatus, an X-ray imaging apparatus having imaging means for capturing an X-ray transmission image formed upon irradiating an object to be inspected with an X-ray generated by said X-ray generating apparatus; and object detecting means for detecting arrival of said object in an imaging area in said X-ray imaging apparatus;

wherein said X-ray generating apparatus comprises:
an X-ray tube for generating, within a housing sealed into vacuum, an X-ray by focusing an electron emitted from a cathode into an anode target by way of a first grid electrode, a second grid electrode, and a focusing electrode;
grid voltage control means for controlling a grid voltage applied to said first grid electrode; and
pulse generating means for generating a pulse which changes from an OFF state to an ON state and maintains said ON state for a predetermined period of time;

wherein said grid voltage control means has cathode current detecting means for detecting a cathode current and, in response to said pulse generated by said pulse generating means, applies a cutoff voltage to said first grid electrode when said pulse is in said OFF state so as to prevent said electron emitted from said cathode from reaching said anode target, and applies to said first grid electrode, in response to said pulse generated by said pulse generating means, a grid operating voltage adjusted such that said cathode current detected by said cathode current detecting means attains a predetermined value when said pulse is in said ON state;

wherein said cathode current detecting means has a cathode current detecting resistor, connected to said cathode, for detecting said cathode current;

wherein said grid voltage control means has:
an operational amplifier having one input terminal for inputting a voltage generated by said cathode current detecting resistor and the other input terminal for inputting a predetermined negative voltage or a reference positive voltage; and
a grid voltage control circuit for controlling, in response to an output from said operational amplifier, said grid voltage applied to said first grid electrode;

wherein said pulse generating means has trigger signal outputting means for outputting a trigger signal according to said detection of said object by said object detecting means and outputs said pulse when said trigger signal is outputted from said trigger signal outputting means; and wherein said imaging means receives said pulse outputted from the pulse generating means and captures said X-ray transmission image when said pulse is in said ON state.

* * * * *